United States Patent
Reitsma

(10) Patent No.: US 10,338,055 B2
(45) Date of Patent: *Jul. 2, 2019

(54) SPECTROGRAPHIC MATERIAL ANALYSIS BASED ON INDUCTIVE SENSING

(71) Applicant: TEXAS INSTRUMENTS INCORPORATED, Dallas, TX (US)

(72) Inventor: George Pieter Reitsma, Redwood City, CA (US)

(73) Assignee: TEXAS INSTRUMENTS INCORPORATED, Dallas, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/678,095

(22) Filed: Aug. 15, 2017

(65) Prior Publication Data

US 2017/0350873 A1 Dec. 7, 2017

Related U.S. Application Data

(63) Continuation of application No. 14/614,234, filed on Feb. 4, 2015, now Pat. No. 9,733,231.

(51) Int. Cl.
*G01N 33/483* (2006.01)
*A61B 5/053* (2006.01)

(52) U.S. Cl.
CPC ........... *G01N 33/483* (2013.01); *A61B 5/053* (2013.01); *A61B 5/0531* (2013.01)

(58) Field of Classification Search
CPC ...... G01N 33/483; A61B 5/053; A61B 5/0531

(Continued)

(56) References Cited

U.S. PATENT DOCUMENTS 6,097,188 A * 8/2000 Sweedler ........... G01R 33/5604
324/318
7,411,390 B2 8/2008 Goldfine et al.
(Continued)

FOREIGN PATENT DOCUMENTS

| GB | 2500216 A | 9/2013 |
| JP | 2002156366 A | 5/2002 |
| WO | 2011038003 A1 | 3/2011 |

OTHER PUBLICATIONS

EU Search Report for Application No. 16747294.3-1115/3286558, dated Apr. 30, 2018.

(Continued)

*Primary Examiner* — Reena Aurora
(74) *Attorney, Agent, or Firm* — Andrew Viger; Charles A. Brill; Frank D. Cimino

(57) ABSTRACT

A multi-frequency inductive sensing system can be used for spectrographic material analysis of a conductive target material (such as tissue) based on electrical impedance spectroscopy. An inductive senor can be driven with an excitation current at multiple sensor excitation frequencies ($\omega$) to project a time-varying magnetic field into a sensing area on the surface of the target material, inducing eddy currents within the target material. The inductive sensor can be characterized by a sensor impedance $Z(\omega)$ as a function of the sensor excitation frequency ($\omega$), and the resulting induced eddy currents. Multiple sensor impedance $Z_s(\omega)$ measurements, at the multiple sensor excitation frequencies ($\omega$), can be determined, which represent electromagnetic properties of the target material (such as permittivity $\epsilon$, permeability $\mu$, and resistivity $\rho$), based on the induced eddy currents. The multiple sensor excitation frequencies ($\omega$), and (Continued)

corresponding multiple sensor impedance $Zs(\omega)$ measurements, can be selected for particular target penetration depths.

20 Claims, 2 Drawing Sheets

(58) Field of Classification Search
USPC .......................................................... 324/234
See application file for complete search history.

(56) References Cited

U.S. PATENT DOCUMENTS

| | | | |
|---|---|---|---|
| 7,696,748 | B2 | 4/2010 | Schliker et al. |
| 9,733,231 | B2* | 8/2017 | Reitsma ............... G01N 33/483 |
| 2001/0019271 | A1* | 9/2001 | Scott ..................... G01N 22/00 |
| | | | 324/637 |
| 2008/0007275 | A1 | 1/2008 | Rubinsky et al. |
| 2008/0211492 | A1 | 9/2008 | Tsukada et al. |
| 2014/0247090 | A1 | 9/2014 | Reitsma |
| 2017/0247090 | A1 | 8/2017 | Danneberg et al. |

OTHER PUBLICATIONS

Madis Ehanurm: "Detection of cerebral edemas and hematomas using eddy currents", Tallinn University of Technology. 2014 /XP002780667, https://digi.lib.ttu.ee/i/file.php?DLID=1105&t=1.

Hughes et al: "Near electrical resonance signal enhancement (NERSE) in eddy-current crack detection", NDT & E International, vol. 66, 2014, pp. 82-89, XP028876548, ISSN:0963-8695, DOI:10.1016/JNDTEINT.2014.04.009.

Hordan, Edward Conrad: "Electromagnetic Waves and Radiating Systems", 1968, Prentice Hall, XP002780668, ISBN:978-0-13-249995-8, pp. 112-161.

* cited by examiner

SPECTROGRAPHIC MATERIAL ANALYSIS BASED ON INDUCTIVE SENSING

CROSS-REFERENCE TO RELATED APPLICATIONS

This application is a continuation of U.S. application Ser. No. 14/614,234, filed 2015 Feb. 4.

BACKGROUND

Technical Field

This Patent Document relates generally to spectrographic analysis of materials, and more particularly to electrical impedance spectroscopy.

Related Art

Electrical impedance spectroscopy is a method of analyzing material properties based on the electrical impedance of the material as a function of the frequency of applied electromagnetic radiation. Applications for electrical impedance spectroscopy include chemical applications such as detecting bacterial growth in food, and medical applications such for tissue and blood analysis.

For example, biological tissues exhibit electrical impedance which varies with frequency. Tissues contain components with both resistive and capacitive (charge storage) properties resulting in a complex electrical impedance. The magnitude of impedance and the dependence of impedance on frequency are both functions of the tissue composition. Measuring the impedance of cells across a range of frequencies will generate a spectrum that is characteristic of the biological tissue. Changes in the impedance spectrum can therefore be directly related to changes in the underlying nature of the tissue.

While this Background information is presented in the context of specific applications of electrical impedance spectroscopy, the present Disclosure is not limited to such applications, but is more generally directed to material analysis based on electrical impedance spectroscopy.

BRIEF SUMMARY

This Brief Summary is provided as a general introduction to the Disclosure provided by the Detailed Description and Drawings, summarizing some aspects and features of the Disclosure. It is not a complete overview of the Disclosure, and should not be interpreted as identifying key elements or features of the invention, or otherwise characterizing or delimiting the scope of the invention disclosed in this Patent Document.

The Disclosure describes apparatus and methods for performing spectrographic material analysis of a target material based on electrical impedance spectroscopy using multi-frequency inductive sensing. For example, the target material can be tissue.

According to aspects of the Disclosure, the methodology for performing spectrographic material analysis of a target material based on electrical impedance spectroscopy using multi-frequency inductive sensing, can include: (a) driving the inductive senor with an excitation current at a sensor excitation frequency ($\omega$); and thereby (b) projecting a time-varying magnetic field into a sensing area on the surface of the target material, inducing eddy currents within the target material. The inductive sensor can be characterized by a sensor impedance $Z(\omega)$ that is a function of the sensor excitation frequency ($\omega$), and the resulting eddy currents induced within the target material. The methodology further includes determining, for multiple sensor excitation frequencies ($\omega$), corresponding multiple sensor impedance $Zs(\omega)$ measurements that represent electromagnetic properties of the target material based on the induced eddy currents. For example, the methodology can be used to determine target electromagnetic properties that are at least one of: permittivity $\varepsilon$, permeability $\mu$, and resistivity $\rho$ (or its inverse conductivity $\sigma$).

According to other aspects of the Disclosure, the multiple sensor excitation frequencies ($\omega$), and corresponding multiple sensor impedance $Zs(\omega)$ measurements, are selected for a target penetration depth, which represent electromagnetic properties of the target material at the target penetration depth. According to other aspects of the Disclosure, the methodology is useable in a resonant inductive sensing system that includes a resonant sensor including a coil inductor, and characterized by a sensor impedance $Rp=L/(C*Rs)$, wherein determining, for multiple sensor excitation frequencies ($\omega$), corresponding multiple sensor impedance $Zs(\omega)$ measurements, is accomplished by: (a) generating a negative impedance that counterbalances sensor resonator impedance $Rp$, such that the generated negative impedance is a function of the eddy currents induced in the target material (which are reflected in sensor resonator impedance $Rp$); and (b) converting the generated negative impedance into sensor response data corresponding to the sensor resonator impedance $Zs(\omega)$ measurements.

Other aspects and features of the invention claimed in this Patent Document will be apparent to those skilled in the art from the following Disclosure.

DETAILED DESCRIPTION

Figure 1:
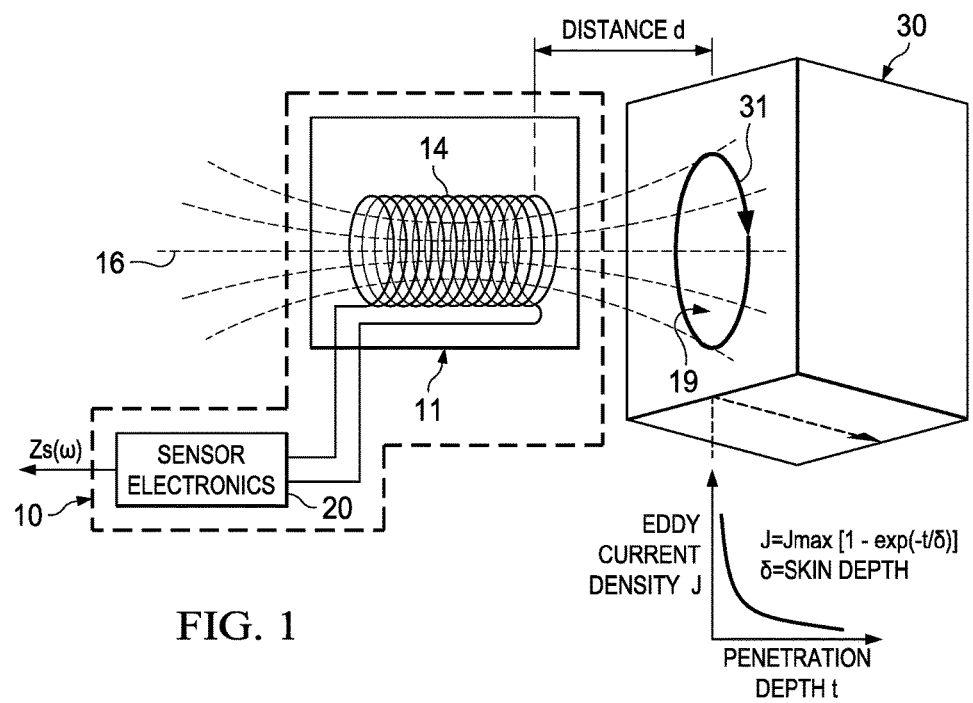
FIG. 1 illustrates an example functional embodiment of an inductive sensing system used for electrical impedance spectroscopy in analyzing electromagnetic properties of a target material (material under test) 30, based on multi-frequency eddy current sensing, including an inductive sensor 10 implemented as a sensor inductor 11 and sensor electronics 20 configured to measure sensor impedance at multiple frequencies, corresponding to electromagnetic properties of the target material.

This Description and the Drawings constitute a Disclosure of example embodiments and applications that illustrate various features and advantages of spectrographic material analysis based on electrical impedance spectroscopy using multi-frequency eddy current sensing to measure electromagnetic properties of a material under test.

A problem addressed by the Disclosure is using electrodes to electrically connect to the material or tissue under test. The contact impedance of electrodes (capacitive or resistive), corrosion, chemical reaction between electrode and the material under test, and repulsion of the electrode by living tissue make the use of electrodes problematic.

In brief overview, aspects of the Disclosure include the use of inductive sensing to measure impedance at multiple frequencies (electrical impedance spectroscopy), based on induced (contactless) eddy current sensing. The multi-frequency impedance measurements are used to determine electromagnetic properties of a target material under test (for example, electrical permittivity ε, magnetic permeability μ, and electrical resistivity ρ (or its inverse electrical conductivity σ)). Example embodiments include an inductive sensing circuit is configured to project a time-varying magnetic field into a sensing area on the surface of the target material, inducing eddy currents within the target material. The inductive sensing circuit includes a sensor including an inductor coil, and sensor electronics configured to drive the sensor inductor coil with an excitation current at a sensor excitation frequency (ω), generating a corresponding time-varying magnetic field projected to the target material. The sensor can be characterized by a sensor impedance Z(ω) that is a function of a sensor excitation frequency (ω), and the resulting eddy currents induced within the target material. The sensor electronics is configured to determine, for multiple sensor excitation frequencies (ω), corresponding multiple sensor impedance Zs(ω) measurements that represent electromagnetic properties of the target material based on the induced eddy currents. In other example embodiments, the multiple sensor excitation frequencies (ω), and corresponding multiple sensor impedance Zs(ω) measurements, are selected for a target penetration depth, which represent electromagnetic properties of the target material at the target penetration depth. In other example embodiments, the inductive sensing circuit is a resonant inductive sensing circuit, including: (a) a sensor resonator including a coil inductor, and characterized by a sensor impedance Rp=L/(C*Rs); and (b) an inductance-to-digital conversion (IDC) unit configured (1) to drive the sensor resonator with a sensor excitation current at a sensor excitation frequency (ω); and (2) to generate a negative impedance that counterbalances sensor resonator impedance Rp, such that the generated negative impedance is a function of the eddy currents induced in the target material (which are reflected in sensor resonator impedance Rp); and (3) to convert the generated negative impedance into sensor response data corresponding to the sensor resonator impedance Zs(ω) measurements.

FIG. 1 illustrates an example functional embodiment of an inductive sensing system used for electrical impedance spectroscopy. An inductive sensor 10 includes a sensor inductor 11 and sensor (readout) electronics 20. Inductive sensor 10 is positioned adjacent a target material under test 30.

Sensor inductor 11 includes a coil 14. Sensor electronics 20 drives a sensor excitation current, with a sensor excitation frequency (ω), through sensor inductor/coil 14, generating a time-varying magnetic field 16, which is projected to target material 30. The longitudinal distance between sensor inductor/coil 14 and the surface of target material 30 is sufficiently short that the magnetic flux generated by the inductor/coil is concentrated within a limited area of the target material surface referred to as a sensing domain 19.

Projected magnetic field 16 induces eddy currents 31 in the surface of the target material 30. Eddy currents 31 consist of displacement current as well conduction current, and hence they depend on the electromagnetic properties of target material being tested, as well as excitation frequency of the magnetic field generated by inductor/coil 14. Eddy currents in the target material result in a power loss in the projected time-varying magnetic field, and in changes in the mutual inductance between the sensor inductor/coil 14 and the eddy currents induced in the target material.

Figure 2:
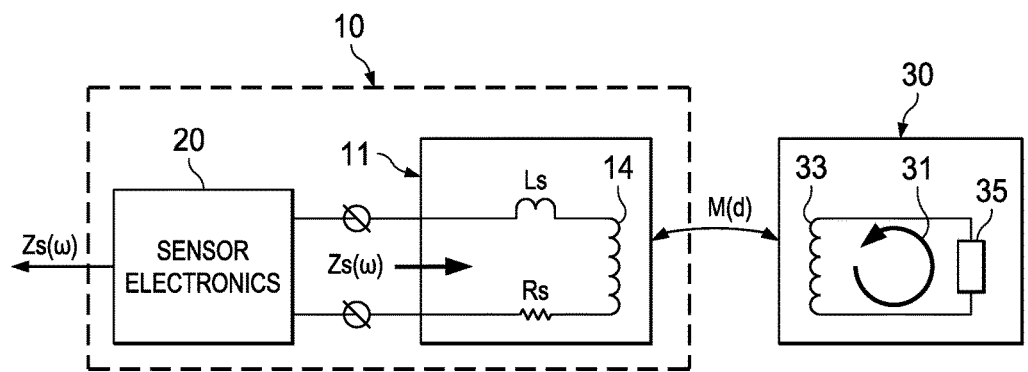
FIG. 2 illustrates an example circuit equivalent embodiment of an inductive sensing system for electrical impedance spectroscopy based on multi-frequency eddy current sensing, including a sensor inductor 11 modeled as a transformer primary side, and the eddy currents 31 induced in target material 30 modeled as a transformer secondary side 33, which is loaded by the impedance 35 of the target material, and including sensor electronics 20 configured to measure sensor impedance at multiple frequencies $Zs(\omega)$.

As described further in connection with FIG. 2, the effects of eddy currents 31 induced in target material 30 are sensed by inductive sensor 10 as sensor impedance Zs(ω), which is a function of the excitation frequency of the time-varying magnetic field 16, and electromagnetic properties of the target material (as reflected in the eddy currents induced in the target material). Eddy current density exponentially decays as it penetrates target material 30, as indicated in FIG. 1. Penetration depth is given by:

$$\delta = \left(\frac{1}{\omega}\right)\left\{\left(\frac{\mu\epsilon}{2}\right)\left[\left(1+\left(\frac{1}{\rho\omega\epsilon}\right)^2\right)^{1/2}-1\right]\right\}^{-1/2} \quad (1)$$

which is a function of sensor excitation frequency ω (rad/sec.), as well as electromagnetic properties of target material 30: electrical permittivity ε, magnetic permeability μ, and electrical resistivity ρ (the inverse of the conductivity σ).

Sensor impedance measurements Rp, corresponding to sensor impedance Zs(ω), are a function of penetration depth given by equation (1).

FIG. 2 illustrates an example circuit equivalent embodiment of the inductive sensing system for electrical impedance spectroscopy based on multi-frequency eddy current sensing.

Inductive sensor 10 includes sensor inductor 11 with inductor/coil 14, which can be represented as a sensor inductance Ls and a loss factor (series resistance Rs).

Sensor inductor 11 can be modeled as the primary side of a transformer. Target material 30 is illustrated as a circuit equivalent, with the induced eddy currents 31 modeled as the secondary side 33 of the transformer, which is loaded by the impedance 35 of the target material under test.

The coupling factor M between primary side 14 and secondary side 33 has a strong dependence on distance (d), and therefore on the penetration depth. This penetration depth, illustrated in FIG. 1 and given by equation (1), has a strong non-linear dependence on function of sensor excitation frequency (ω).

Therefore the electromagnetic properties of target material 30 can be determined by measuring the sensor impedance Zs(ω) at multiple sensor excitation frequencies (ω), and solving for permittivity ε, permeability μ, and resistivity ρ (or its inverse conductivity σ):

$$\left.\begin{array}{c}Zs(\omega 1) = F(\omega 1, \varepsilon, \sigma, \mu, d, Ls, Rs) \\ \vdots \\ Zs(\omega n) = F(\omega n, \varepsilon, \sigma, \mu, d, Ls, Rs)\end{array}\right\} \quad (2)$$

To extract electrical parameters (like permittivity and resistivity), the multi-frequency sensor impedance Zs(ω) measurements can be near a frequency corresponding to a particular penetration depth within the target material. For example, for a target penetration depth corresponding to a lower frequency measurement around 10 MHz, sensor impedance Zs(ω) measurements around 9 MHz and 11 MHz can be used, while for a target penetration depth corresponding to a higher frequency measurement around 100 MHz, sensor impedance $Zs(\omega)$ measurements around 95 MHz and 105 MHz can be used.

Note that, because measuring the sensor impedance $Zs(\omega)$ at multiple frequencies induces eddy currents at different skin (penetration) depths, inductive sensing based on multi-frequency eddy current sensing can be used for spectrographic analysis at different target penetration depths within the target material, such as different tissue depths. For example, in the case of spectrographic analysis of a tissue target, at higher frequencies (such as 100 Mhz), eddy currents are confined to the upper tissue layer (penetration depth is less), and therefore sensor impedance $Zs(\omega)$ measurements only observe this upper tissue layer. At a lower frequency (such as 10 MHz), the skin (penetration) depth becomes larger, hence eddy currents run deeper, so sensor impedance $Zs(\omega)$ measurements observe less of the upper tissue layer, and more of the deeper tissues.

A calibration cycle can be used to eliminate frequency dependent behavior of the material analysis system, such as where the electromagnetic properties of the target material under test have a frequency dependent behavior.

A number of advantages derive from spectrographic material analysis based on electrical impedance spectroscopy using multi-frequency eddy current sensing. Inductive sensing is contactless (noninvasive), avoiding electrode contacts to a material under test, and thereby avoiding chemical or corrosive interaction. A concentrated projected sense field can be used for a concentrated sensing area. An insulator can be used between the material/object/tissue under test.

Figure 3:
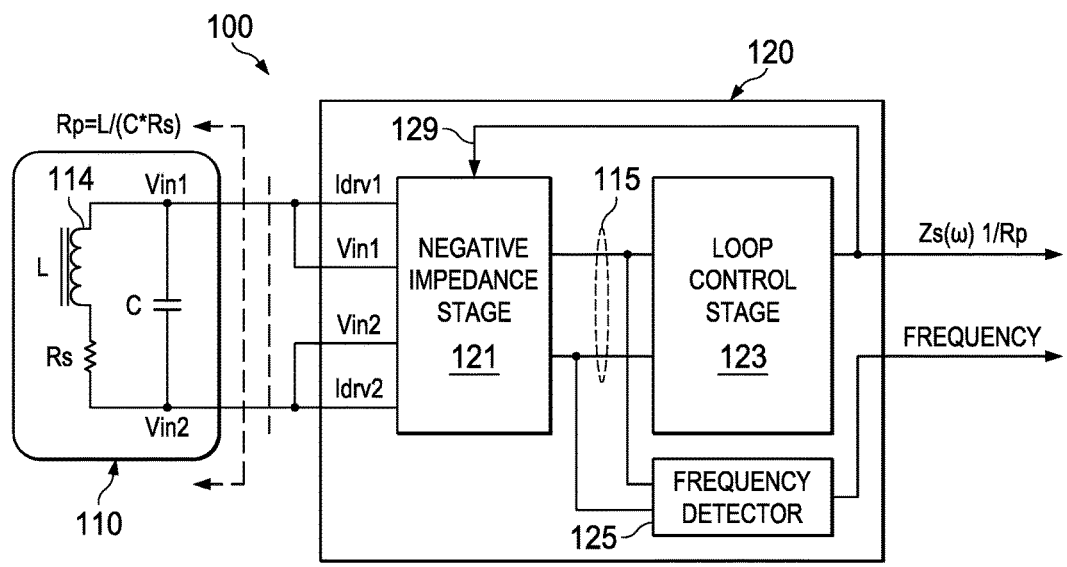
FIG. 3 illustrates an example embodiment of a resonant inductive sensor system that includes an LC resonator 110, driven by an inductance-to-digital (IDC) conversion unit 120 that includes a negative impedance stage 121 driving excitation current with a negative impedance, and a loop control stage 123 that provides a feedback loop control signal 129 that controls negative impedance.

FIG. 3 illustrates an example embodiment of a resonant inductive sensor 100 that can be used for measuring sensor impedance $Zs(\omega)$ based on eddy current sensing, and therefore for spectrographic material analysis based on electrical impedance spectroscopy, using multi-frequency eddy current sensing.

Resonant inductive sensor 100 includes an LC sensor resonator 110 and an inductance-to-digital conversion (IDC) unit (sensor electronics) 120. Sensor resonator 110 includes a coil inductor 114, and is characterized by a resistive loss factor Rs, or the circuit equivalent parallel sensor impedance $Rp=L/(C*Rs)$, which takes into account LC reactive impedance (frequency dependent).

Eddy current sensing for spectrographic material analysis will cause a change in resonator impedance (loss factor Rp) based on electromagnetic properties of a target material under test. This change in resonator impedance $Zs(\omega)$, is converted by IDC 120 into sensor response data 1/Rp, corresponding to the electromagnetic properties of the target material.

IDC 120 determines resonator impedance $Zs(\omega)$ based on the negative impedance that counterbalances the positive resonator impedance Rp. Specifically, IDC 120 drives resonator 110 with an AC sensor excitation current, with a sensor excitation frequency ($\omega$) synchronized with the oscillation frequency of the resonator. IDC 120 establishes a negative impedance control loop that drives resonator 110 with a negative impedance to maintain sustained resonator oscillation by counterbalancing resonator impedance Rp (loss factor).

The example IDC 120 includes a negative impedance stage 121 and a loop control stage 123. Negative impedance stage 121, interfaced to sensor resonator 110, drives resonator excitation current Idrv1/Idrv2 with a loop-controlled negative impedance, synchronized with resonator oscillation voltage Vin1/Vin2. Loop control stage 123 monitors average resonator oscillation amplitude (115), and provides a feedback loop control signal 129 that controls negative impedance to maintain sustained resonator oscillation (in the example IDC, corresponding to maintaining a substantially constant average resonator oscillation amplitude).

That is, the IDC resonant sensor circuit 120 establishes a negative impedance control loop (121/123), that drives the sensor resonator (Idrv1/Idrv2) with a controlled negative impedance (129), that controls average resonator oscillation amplitude to sustain resonator oscillation. The controlled negative impedance balances resonator impedance Rp (loss factor) for sustained resonator oscillation.

The example IDC 120 includes a frequency detector 125 that measures the resonator oscillation frequency for sensor resonator 110. For example, frequency detector 125 can be implemented with a frequency counter. Resonator oscillation frequency can be used to determine inductance for sensor resonator 110 (coil inductor 114), based on the reactive part of the sensor impedance. Resonance frequency changes in response to a change in the reactive part of sensor impedance Rp.

IDC 120 outputs sensor response data (1/Rp), corresponding to sensor impedance $Zs(\omega)$, and frequency. $Zs(\omega)$ (1/Rp) corresponds to the loop control signal 129 that controls negative impedance that counterbalances sensor impedance Rp. That is, the sensor response data output from IDC 120 quantifies changes in negative impedance that counteract changes in resonator impedance $Zs(\omega)$ (loss factor).

Resonator impedance $Zs(\omega)$ (1/Rp=C/L*Rs), including the reactive part of the sensor impedance, reflects the total impedance of the sensor. As such, the multi-frequency resonator impedance $Zs(\omega)$ measurements can be used to determine electromagnetic properties of the target material under test. In particular, while metal targets are inductive, that is not the case for non-metallic conductive targets such as tissue.

Note that IDC resolution is a significant factor in determining coil diameter. For an example 10 bit IDC, frequency and coil size should be chosen such that the coil diameter is in the range of 5% to 10% of the skin depth.

The Disclosure provided by this Description and the Figures sets forth example embodiments and applications illustrating aspects and features of the invention, and does not limit the scope of the invention, which is defined by the claims. Known circuits, functions and operations are not described in detail to avoid obscuring the principles and features of the invention. These example embodiments and applications can be used by ordinarily skilled artisans as a basis for modifications, substitutions and alternatives to construct other embodiments, including adaptations for other applications.

The invention claimed is:

1. A system for spectrographic material analysis of a conductive target material based on inductive sensing, the system comprising:
   a sensor including an inductor coil; and
   an inductance-to-data converter (IDC) coupled to the sensor,
   to drive the sensor inductor coil with an excitation current at a selectable sensor excitation frequency ($\omega$),
   to generate a magnetic sensing field projected into a pre-defined sensing area,
   the magnetic sensing field to induce eddy currents within a conductive target material introduced for spectrographic material analysis within the sensing area, and to determine, for each generated magnetic sensing field at a selected sensor excitation frequency ($\omega$), a property of the driven sensor inductor coil corresponding sensor impedance $Zs(\omega)$;

the sensor impedance $Zs(\omega)$ being a function of the sensor excitation frequency ($\omega$), and a response of the driven sensor coil to induced eddy currents.

2. The system of claim 1, for a conductive target material introduced within the pre-defined sensing area:

the IDC to determine, for multiple sensor excitation frequencies ($\omega$), corresponding multiple sensor impedance $Zs(\omega)$ measurements that represent electromagnetic properties of the target material based on the corresponding induced eddy currents.

3. The system of claim 2, wherein the electromagnetic properties are at least one of: permittivity $\epsilon$, permeability $\mu$, and resistivity $\rho$ (or its inverse conductivity $\sigma$).

4. The system of claim 1, wherein each sensor impedance measurement $Zs(\omega)$ is a function of the induced eddy current and associated target penetration depth:

$$\delta = \left(\frac{1}{\omega}\right)\left\{\left(\frac{\mu\epsilon}{2}\right)\left[\left(1+\left(\frac{1}{\rho\omega\epsilon}\right)^2\right)^{1/2}-1\right]\right\}^{-1/2}$$

which is a function of sensor excitation frequency ($\omega$), and electromagnetic properties of the target material: electrical permittivity $\epsilon$, magnetic permeability $\mu$, and electrical resistivity $\rho$ (the inverse of the conductivity $\sigma$).

5. The system of claim 4, wherein the multiple sensor excitation frequencies ($\omega$), and corresponding multiple sensor impedance $Zs(\omega)$ measurements, are selected for a target penetration depth, which represent electromagnetic properties of the target material at the target penetration depth.

6. The system of claim 1, wherein the IDC is based on resonant inductive sensing, including:

a sensor resonator including a coil inductor, and characterized by a sensor impedance $Rp=L/(C*Rs)$; and the IDC to drive the sensor resonator with a sensor excitation current at a sensor excitation frequency ($\omega$); and to generate a negative impedance that counterbalances sensor resonator impedance Rp, such that the generated negative impedance is a function of the eddy currents induced in the target material (which are reflected in sensor resonator impedance Rp); and to convert the generated negative impedance into sensor response data corresponding to the sensor resonator impedance $Zs(\omega)$ measurements.

7. The system of claim 1, wherein the target material is tissue.

8. A circuit for use in a system for spectrographic material analysis of a conductive target material based on inductive sensing, the circuit for use with a sensor including an inductor coil, the circuit comprising:

an inductance-to-data converter (IDC) coupled to the sensor, to drive the sensor inductor coil with an excitation current at a selectable sensor excitation frequency ($\omega$), to generate a magnetic sensing field projected into a pre-defined sensing area, the magnetic sensing field to induce eddy currents within a conductive target material introduced for spectrographic material analysis within the sensing area, and to determine, for each generated magnetic sensing field at a selected sensor excitation frequency ($\omega$), a property of the driven sensor inductor coil corresponding sensor impedance $Zs(\omega)$;

the sensor impedance $Zs(\omega)$ being a function of the sensor excitation frequency ($\omega$), and a response of the driven sensor coil to induced eddy currents.

9. The circuit of claim 8, for a conductive target material introduced within the pre-defined sensing area:

the IDC to determine, for multiple sensor excitation frequencies ($\omega$), corresponding multiple sensor impedance $Zs(\omega)$ measurements that represent electromagnetic properties of the target material based on the corresponding induced eddy currents.

10. The circuit of claim 9, wherein the electromagnetic properties are at least one of: permittivity $\epsilon$, permeability $\mu$, and resistivity $\rho$ (or its inverse conductivity $\sigma$).

11. The circuit of claim 8, wherein each sensor impedance measurement $Zs(\omega)$ is a function of the induced eddy current and associated target penetration depth:

$$\delta = \left(\frac{1}{\omega}\right)\left\{\left(\frac{\mu\epsilon}{2}\right)\left[\left(1+\left(\frac{1}{\rho\omega\epsilon}\right)^2\right)^{1/2}-1\right]\right\}^{-1/2}$$

which is a function of sensor excitation frequency ($\omega$), and electromagnetic properties of the target material: electrical permittivity $\epsilon$, magnetic permeability $\mu$, and electrical resistivity $\rho$ (the inverse of the $\sigma$).

12. The circuit of claim 11, wherein the multiple sensor excitation frequencies ($\omega$), and corresponding multiple sensor impedance $Zs(\omega)$ measurements, are selected for a target penetration depth, which represent electromagnetic properties of the target material at the target penetration depth.

13. The circuit of claim 8, wherein the IDC is based on resonant inductive sensing, including:

a sensor resonator including a coil inductor, and characterized by a sensor impedance $Rp=L/(C*Rs)$; and the IDC to drive the sensor resonator with a sensor excitation current at a sensor excitation frequency ($\omega$); and to generate a negative impedance that counterbalances sensor resonator impedance Rp, such that the generated negative impedance is a function of the eddy currents induced in the target material (which are reflected in sensor resonator impedance Rp); and to convert the generated negative impedance into sensor response data corresponding to the sensor resonator impedance $Zs(\omega)$ measurements.

14. The circuit of claim 8, wherein the target material is tissue.

15. A method of performing spectrographic material analysis of a target material based on electrical impedance spectroscopy, the method suitable for use in an inductive sensing system that includes an inductive sensor with a coil inductor, comprising driving the inductive senor with an excitation current at a sensor excitation frequency ($\omega$); and thereby projecting a time-varying magnetic field into a sensing area on the surface of the target material, inducing eddy currents within the target material;

wherein the inductive sensor is characterized by a sensor impedance $Z(\omega)$ that is a function of the sensor excitation frequency ($\omega$), and the resulting eddy currents induced within the target material; and determining, for multiple sensor excitation frequencies (ω), corresponding multiple sensor impedance Zs(ω) measurements that represent electromagnetic properties of the target material based on the induced eddy currents.

16. The method of claim 15, wherein the electromagnetic properties are at least one of: permittivity ε, permeability μ, and resistivity ρ (or its inverse conductivity σ).

17. The method of claim 15, wherein each sensor impedance measurement Zs(ω) is a function of the induced eddy current and associated target penetration depth:

$$\delta = \left(\frac{1}{\omega}\right)\left\{\left(\frac{\mu\epsilon}{2}\right)\left[\left(1 + \left(\frac{1}{\rho\omega\epsilon}\right)^2\right)^{1/2} - 1\right]\right\}^{-1/2}$$

which is a function of sensor excitation frequency (ω), and electromagnetic properties of the target material: electrical permittivity ε, magnetic permeability μ, and electrical resistivity ρ (the inverse of the conductivity σ).

18. The method of claim 17, wherein the multiple sensor excitation frequencies (ω), and corresponding multiple sensor impedance Zs(ω) measurements, are selected for a target penetration depth, which represent electromagnetic properties of the target material at the target penetration depth.

19. The method of claim 15, wherein the method is useable in a resonant inductive sensing system that includes a resonant sensor including a coil inductor, and characterized by a sensor impedance Rp=L/(C*Rs), and:

wherein determining, for multiple sensor excitation frequencies (ω), corresponding multiple sensor impedance Zs(ω) measurements, is accomplished by:

generating a negative impedance that counterbalances sensor resonator impedance Rp, such that the generated negative impedance is a function of the eddy currents induced in the target material (which are reflected in sensor resonator impedance Rp); and converting the generated negative impedance into sensor response data corresponding to the sensor resonator impedance Zs(ω) measurements.

20. The method of claim 15, wherein the target material is tissue.

* * * * *